United States Patent [19]

Karagozler et al.

[11] Patent Number: 5,258,111
[45] Date of Patent: Nov. 2, 1993

[54] IODINE DOPED POLYTHIENYLENE COATED ELECTRODE

[75] Inventors: A. Ersin Karagozler; Harry B. Mark, Jr.; Hans Zimmer; Ahmed Galal, all of Cincinnati, Ohio

[73] Assignee: University of Cincinnati, Cincinnati, Ohio

[21] Appl. No.: 664,333

[22] Filed: Mar. 4, 1991

[51] Int. Cl.$^5$ ............................................. G01N 27/26
[52] U.S. Cl. ................................... 204/416; 204/418; 204/419; 204/153.13
[58] Field of Search ............... 204/416, 418, 419, 282, 204/153.13, 413, 420

[56] References Cited

U.S. PATENT DOCUMENTS 5,139,626 8/1992 Yamaguchi et al. ................ 204/416

OTHER PUBLICATIONS

Teasdale, P., et al., Electroanalysis 1:541-547 (1989).
Lee, I., et al., J. Chem. Soc., Chem. Commun. 8:497-498 (1989).
Yamamoto, T., et al., J. Polym. Sci., Polym. Let. Ed. 18:9-12 (1980).
Czerwinski, A., et al, J. Chem. Soc., Chem. Commun. 587:1158-1159 (1985).
Yano, Jr., et al., Chemistry Letters, pp. 1943-1946 (1988).

Primary Examiner—John Niebling
Assistant Examiner—Patrick J. Igoe
Attorney, Agent, or Firm—Dressler, Goldsmith, Shore, Sutker & Milnamow, Ltd.

[57] ABSTRACT

An iodide-doped, polythienylene coated electrode suitable for a potentiometric iodide ion sensor and a method for its manufacture are disclosed. The electrode is prepared by polymerizing the polythienylene on a working surface thereof. To this end, the working surface is contacted with a monomer solution of thiophene monomer and an electrolyte dissolved in organic solvent. Thereafter the solution is subjected to either a substantially constant potential of about 1.6 volts to about 1.8 volts vs. Ag/AgCl or to a cycling potential between −0.1 volts and +1.8 volts vs. Ag/AgCl for a time period sufficient to polymerize a polythienylene film of the desired thickness onto the working surface of the electrode.

The polythienylene film on the working surface is then doped with $I_2$ by placing the coated electrode in an aqueous solution of iodide salt under applied potential conditions of about +0.6 volts to about +1 volt vs. Ag/AgCl for a period of time sufficient to dope the polymer. The period of time is dependent upon the thickness of the film applied to the electrode. The produced electrode usually exhibits a response of about 55 mV/decade to about 65 mV/decade in iodide solutions with a molar iodide ion concentration of about $10^{-1}$ to about $10^{-7}$.

11 Claims, 3 Drawing Sheets

IODINE DOPED POLYTHIENYLENE COATED ELECTRODE

TECHNICAL FIELD

The invention is directed to a conductive polymer-coated electrode doped with iodine, and to a method for making the electrode. This electrode can be used in a potentiometric iodide ion sensor for electrochemical analysis.

BACKGROUND OF THE INVENTION

For electrochemical analysis chemically modified electrodes offer distinct advantages over electrodes with an unmodified working surface. They are more selective. Therefore, surface fouling by precipitation or adsorption of ions other than those of interest is avoided by their use. Chemically modified electrodes also require the application of an overpotential in order to drive electrochemical reactions.

Synthesis of a self-doped conducting polymer, polyaniline, is disclosed in Epstein, Arthur J., "Synthesis of Self-Doped Conducting Polyaniline" *Journal of the American Chemical Society*, 112:2800–2801 (1990). Although doping has been recognized a enhancing the conductivity of conducting polymers, the use of a doped polymer as a surface modifier for an electrode to facilitate chemical analysis has not been heretofore recognized.

Undoped conducting polymers, on the other hand, have been used as surface modifiers of electrodes with mixed results. For example, a poly(3-methylthiophene)-coated electrode was stated to be useful for the detection of chromium (VI) at low levels in Teasdale, P., et al., "Selective Determination of Cr(VI) Oxyanions Using a Poly-3-methylthiophene-modified Electrode," *Electroanalysis*, 1:541–547 (1989). The detection of chromium ion was observed by preconcentrating the Cr(VI) ion within the polymer matrix. The selectivity of the polymer for Cr(VI) ion was said to be caused by the presence of the cation from the electrolyte used in the electrodeposition of the polymer onto the electrode, which may have been incorporated into the polymer matrix. The detection of the Cr(VI) was accomplished by cyclic voltammetry. The electrochemical mechanism which formed the basis for the detection of the Cr(VI) was reported to be non-Nernstian. The electrode also exhibited a degradation in performance after repeated use. Moreover, the experimental results were not reproducible from electrode to electrode.

In Lee, I., et al., "Aggregation of Bu$_4$NClO$_4$ Electrolyte in the Presence of Dicyclohexano-18-crown-6 in Poly(3-methyl-thiophene) Conducting Polymer Film Electrodes. Unusual Transient Current Phenomena," *J. Chem. Soc. Chem. Commun.*, 8:497–498 (1989) voltammograms of a poly(3-methylthiophene)-coated electrode in a Bu$_4$NClO$_4$-dicyclohexano-18-crown-6 acetonitrile solution has been reported. The obtained voltammograms were said to exhibit up and down fluctuations caused by the doping and undoping of the poly(3-methyl-thiophene) coating in the solution. Use of the electrodes to detect the presence of a specific ionic species in solution was not reported.

The preparation of iodine-doped and copper-doped poly(thiophene-2,5-diyl) are disclosed in Yamamoto, T., et al., "Preparation of Thermostable and Electric-Conducting Poly(2,5-Thienylene)," *J. Polym. Sci., Polym. Let. Ed.*, 18:9–12 (1980) and in Czerwinski, A., et al, "The Effect of 'Water and Transition Metal Ion Doping' on the Conductivity of Poly(3-substituted Thiophene-2,5 diyls)," *J. Chem. Soc. Commun.*, 587:1158–1159 (1985). However, their suitability for performing sensitive electrochemical measurements, such as the detection of an ionic species in solution, has not been reported.

In Yano, Jr., et al., "Selective Nernstian Response of Poly(N,N-dimethylaniline))/Poly(o-chloroaniline) Dual-layer coated Electrode to Dissolved Iodide Ion," *Chemistry Letters* pp. 1943–1946 (1988) an electrode with a dual layer coated electrode was observed to be selective for the detection of I$^-$ion in solution. The first polymer layer was doped in a 0.1M potassium iodide solution before the second layer was applied thereon and the second layer was observed to contribute to the selectivity of the electrode measurements.

It has now been found that ion doped organic conducting polymers such as polythienylenes and the like can be used as surface modifiers of electrode surfaces for sensitive and selective electrochemical measurements. The electronic properties of such conducting polymers can be reversibly controlled by the doping and undoping of the polymer. Therefore, the conductivity of such polymers can be turned on and off as desired.

Such electrodes are useful to detect the presence of trace amounts of ionic species in solution. The advantages of an electrode with a surface coated with doped poly(thiophene) capable of performing sensitive ion detection for potentiometric analysis has heretofore gone unrecognized.

SUMMARY OF THE INVENTION

An electrode having a doped, conductive polymer-coated working surface and a method for its manufacture are disclosed. The working surface of the electrode is made of an inert material such as graphite, glassy carbon, platinum, tin oxide and the like. Polythienylene is such a conductive polymer and is polymerized onto the working surface from a solution of a thiophene monomer and an electrolyte in organic solvent to provide a coating thickness in the range of about 200 Å to about 3000 Å, preferably about 500 Å to about 2000 Å, and then doped. The thiophene monomer can be an alkyl thiophene, preferably 3-methyl thiophene, and is present in the monomer solution at a concentration of about 0.05M to about 0.1M. Suitable electrolytes include tetrabutylammonium fluoroborate, lithium perchlorate, tetrabutylammonium sulfite, and the like. The concentration of electrolyte in the monomer solution is about 0.01M to about 1M. Suitable organic solvents are acetonitrile, benzonitrile, methyl chloride, tetrahydrofuran and the like.

To polymerize the thiophene monomer onto the working surface, the working surface is placed in the monomer solution under constant potential conditions of about 1.6 volts to about 1.8 volts, preferably about +1.65 volts vs. Ag/AgCl for about 30 to about 120 seconds. The thiophene monomer can also be polymerized onto the working surface of the electrode by placing the working surface into a monomer solution as described above and then subjecting the solution to a potential cycled in the range of about −0.1 volts to about +1.8 volts vs. Ag/AgCl for a time period of about 30 to about 90 seconds. The resulting polythienylene film thickness on the electrode usually is about 500 Å to about 2000 Å.

The deposited polythienylene coating is then doped with a desired element e.g., iodine ($I_2$), by placing the electrode bearing the polythienylene-coated working surface in an aqueous solution of an iodide salt. The iodide salt can be an alkali metal iodide salt, preferably a potassium iodide salt. The iodide salt concentration can be about $10^{-1}$M to about $10^{-3}$M. The iodide is simultaneously oxidized and doped into the polythienylene polymer matrix. This is achieved by subjecting the iodide salt solution to a potential of about +0.6 volts to about +1 volt vs. Ag/AgCl, preferably about +0.7 volts, for about 15 to about 600 seconds while the electrode is immersed therein.

The iodine-doped, polythienylene-coated electrode produced in the foregoing manner usually exhibits a substantially Nernstian response of about 55 mV/decade to about 65 mV/decade when placed in aqueous iodide salt solutions with iodide concentrations of about $10^{-1}$M to about $10^{-7}$. Such a response is well suited as the basis for a sensitive and selective potentiometric analysis for the presence of iodide ion in solution.

DETAILED DESCRIPTION OF PREFERRED EMBODIMENTS

Figure 1:
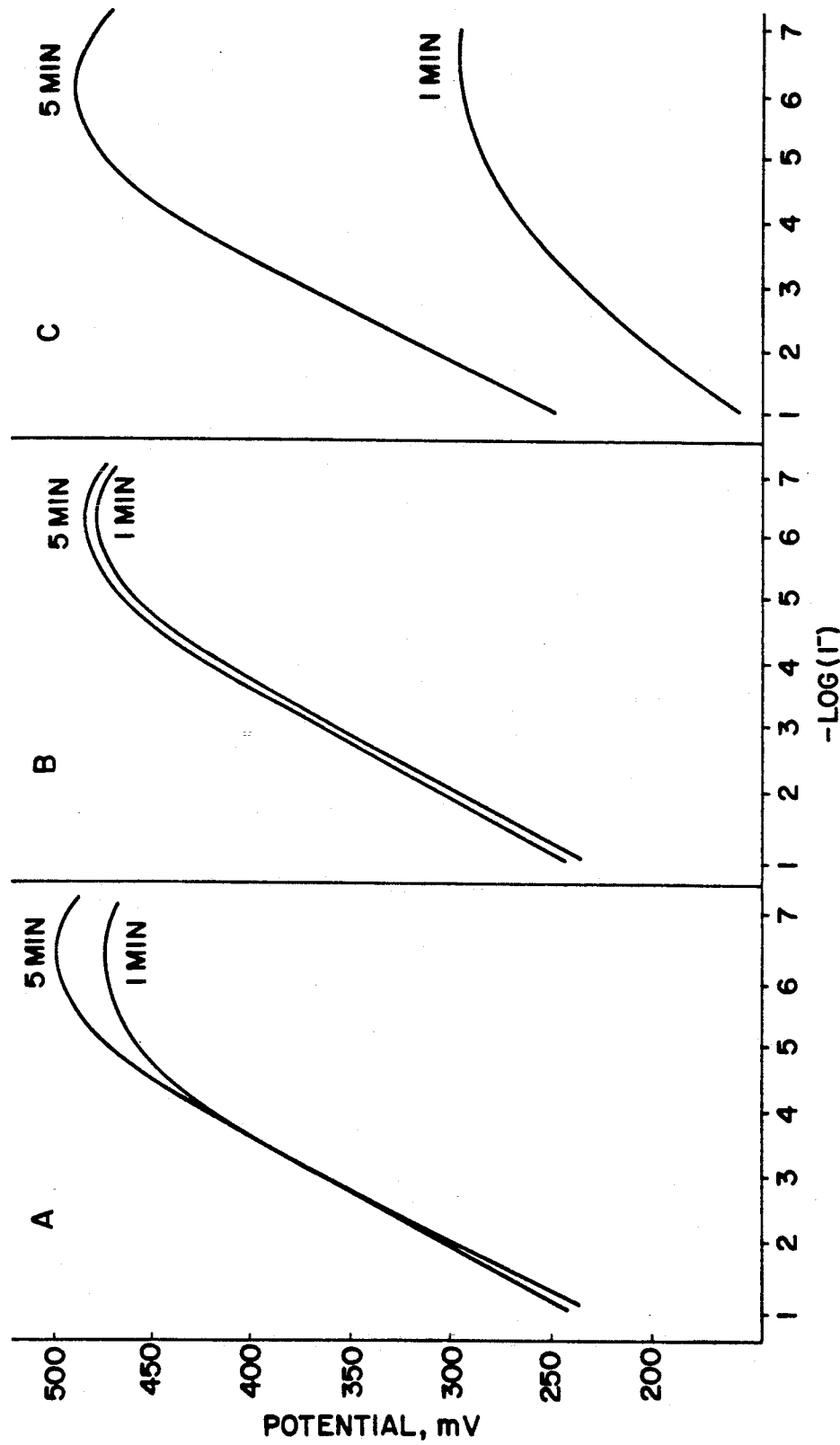
FIG. 1 illustrates the effect of the doping period on the response of three electrodes (A, B and C) coated with poly-3-methyl-2,5-thienylene of varying thickness.

Conducting polymers can be utilized to chemically modify electrode surfaces to enhance the ability of the electrode to perform sensitive and selective chemical measurements. Suitable conducting polymers are electrochemically synthesized in oxidized form and are then doped with anions. The ions with which the polymers are initially doped are obtained from the electrolyte in which the electrochemical polymerization is conducted.

Electrochemically synthesized conducting polymers that have been doped can be switched to a neutral state, i.e. a nonconducting or undoped state, either by scanning with a negative potential or by applying a constant negative potential.

This ability of electrochemically synthesized conducting polymers to be doped and undoped can form the basis for a potentiometric analysis. In such a potentiometric analysis, the electrical potential of an indicator electrode, which is in equilibrium with the electrons in the system, is measured against a reference electrode.

To make a conductive polymer film, such as a polythienylene film, suitable as a coating for a selective iodide ion sensor electrode in a potentiometric analyzer, the polymer is formed as a film on the working electrode and the film is doped with iodine. This film is prepared by first electropolymerizing a thiophene monomer onto a working surface of a base electrode. The working surface of the electrode can be provided by a conductive but chemically neutral, i.e., inert, material such as platinum, graphite, glassy carbon, tin oxide and the like. The preferred working surface material is graphite. The polymeric coating thickness on the electrode working surface varies with duration of the electropolymerization and usually is in the range of about 200 Angstroms (Å) to about 3,000 Å, preferably about 500 Å to about 2,000 Å.

The working surface material does not participate in the oxidation/reduction reaction (Redox) that occurs at the electrode surface. The base electrode has an electrically conductive metal wire, preferably a copper wire, affixed thereto or some other electrically conductive means that conducts electrons from the base electrode to the potentiometric sensor.

The thiophene monomer is polymerized onto the working surface in a single compartment, three electrode cell together with a solution of the thiophene monomer and substantially inert electrolyte. The solvent is an organic solvent. The thiophene monomer is present in a molar concentration of about 0.05M to about 0.1M. The electrolyte is present in a molar concentration of about 0.01M to about 1M. Preferably, the monomer-to-electrolyte concentration ratio is in the range of about 1:5 to about 1:10. The base electrode functions as the working electrode in this single compartment cell. The other two electrodes employed in the three-electrode system can be a platinum electrode as a counter electrode and an Ag/AgCl electrode as a reference electrode.

The thiophene monomer can be a 3-alkyl thiophene monomer wherein the alkyl group has 1 to 4 carbon atoms. Preferably, the 3-alkyl thiophene monomer is 3-methyl thiophene; however, other monomers that can be polymerized to dopable, conductive polymer films can also be employed.

Typical electrolytes suitable for present purposes are the tetrabutyl-ammonium salts and lithium salts of tetrafluoroborate ($BF_4^-$), hexafluoro phosphate ($PF_6^-$), trifluorocarbonate ($CF_3^-$), sulfite ($SO_3^-$) perchlorate ($ClO_4^-$) and the like. The preferred electrolyte is tetrabutylammonium tetrafluoroborate.

The electrolyte and monomer are dissolved in a water-soluble solvent that does not interact with the monomer and does not dissociate at the applied voltage. Illustrative are solvents such as acetonitrile, benzonitrile, methyl chloride, tetrahydrofuran and the like.

The thiophene monomer is electropolymerized onto the base electrode in one of two ways. The thiophene is polymerized under constant potential conditions of about 1.6 volts to about 1.8 volts, preferably about +1.65 volts vs. an Ag/AgCl reference electrode, or under repeated controlled potential cycles in the range of about −0.1 volts to about +1.8 volts, again vs. an Ag/AgCl reference electrode.

After the electrodeposition of the polymer onto the electrode, the electrode is then rinsed, dried and immersed in an aqueous iodide salt solution contained in another three-electrode single compartment cell for doping. The iodide salt can be an alkali metal salt, preferably potassium iodide. The concentration of iodide salt in solution is about 0.1M to about 0.001M, preferably about 0.01M.

The polythienylene film and the iodide ion are preferably both in the oxidized state, thus the iodine is oxidized and simultaneously doped into the polymer. Potentials of about +0.6 volts to about +1 volts, preferably about +0.7 volts, all voltages vs. an Ag/AgCl electrode, accomplish this objective.

In one embodiment, the potentials were determined by first calculating the oxidation potential of a solution with a given iodide ion concentration at an inert electrode such as platinum. These standard electrode potential of the $I_2(s)/I^-$ couple, 0.535 volts, was used as a base, and the potential of the Ag/AgCl (3M NaCl) reference electrode was approximated to that of a saturated KCl electrode which is 0.197 volt.

The oxidation potential range of solutions with an iodide ion ($I^-$) concentration of 0.1M to 0.001M at a platinum electrode was calculated to be about 0.673 volts to about 0.555 volts. Since oxidation potential values of an iodide solution at a poly-3-methyl-2,5-thienylene coated electrode are shifted to more positive potentials than those of the same solution at a platinum electrode, the doping potential of iodide into the polythienylene coating on the electrode was adjusted accordingly. Furthermore, since a second iodide oxidation peak has been observed to occur around +1.0 volt using cyclic voltammetry, a doping potential of less than +1.0 volt is preferred and was used.

In order to ensure adequate electrode performance, the effect of polymer thickness and the extent to which the polymer is doped on electrode performance were determined. The effect of these parameters on overall electrode performance is discussed hereinbelow.

Electrodes coated with poly-3-methyl-2,5-thienylene for 60 seconds and doped in an aqueous solution of potassium iodide ($10^{-2}$M KI) at different voltages produced different calibration curves. An electrode doped at +1.5 volts did not produce an acceptable calibration curve. The electrodes doped at +1.0 volts and +0.5 volts did, however, produce acceptable calibration curves.

The change in the log of iodide concentration in solutions versus the corresponding change in potential, which is the slope of the response curve, preferably is substantially constant so that a change in ion concentration can be easily calculated from the observed change in electrical potential. The slope of the +1.0 volt-doped calibration curve was observed to be 56.6 mV/decade and the slope of the +0.5 volt-doped calibration curve was observed to be 49.2 mV/decade. The correlation coefficients of the data for the two doping procedures were 0.996 and 0.997, respectively.

As stated above, since a second iodide oxidation peak occurs at about +1 volt, according to cyclic voltammetry, a potential of less than +1 volt is preferred for doping the iodine into the polymer.

The thickness of the polythienylene coating on the electrode also influences the response of the electrode. Although polythienylene coated electrodes with film thickness obtained with coating times of 30 seconds, 60 seconds and 90 seconds all produce acceptable calibration curves, the electrode with the relatively thinnest coating (30s) has the most predictable response over the widest range of iodide ion concentrations. This is illustrated in FIG. 1.

The effects of electroactivation parameters on correlation coefficients and the slopes of calibration curves for various concentration ranges are illustrated in Table 1, below.

To obtain the above data, electrodes with a poly-3-methyl-2,5-thienylene coating were doped in aqueous solutions of potassium iodide of varying concentration. The doping potential was +0.7 volt. This potential was applied vs. Ag/AgCl for a predetermined time period. An increase in the dopant concentration was observed to actually decrease the iodide ion concentration range of solutions in which the coated electrode had a constant slope, i.e. a response to concentration change predicted by the Nernst equation. The range in which the electrode has this constant slope is defined as the working range of the electrode.

TABLE 1

IMPACT OF ELECTROACTIVATION PARAMETERS ON THE CORRELATION COEFFICIENTS (R)[1] AND SLOPE (S)[2] OF CALIBRATION CURVES FOR VARIOUS CONCENTRATION RANGES

| | RANGE OF MOLAR IODIDE ($I^-$) CONCENTRATION | | | | | |
|---|---|---|---|---|---|---|
| | $10^{-1}$ to $10^{-4}$ | | $10^{-1}$ to $10^{-5}$ | | $10^{-1}$ to $10^{-6}$ | |
| | R | S | R | S | R | S |
| Film Deposition Time (seconds) | | | | | | |
| 30 | 1 | 62 | 1 | 60.9 | 0.993 | 55.5 |
| 60 | 1 | 60.2 | 1 | 59.5 | 0.993 | 53.9 |
| 90 | 1 | 59.9 | 1 | 59.5 | 0.993 | 53.9 |
| Dopant (KI) Conc. (M) | | | | | | |
| 0.1 | 0.999 | 62 | 0.993 | 55.6 | 0.982 | 48.7 |
| 0.01 | 1 | 62.5 | 1 | 61.9 | 0.998 | 58.5 |
| 0.001 | 1 | 62.3 | 1 | 63.1 | 1 | 62.3 |
| Doping Period (seconds) | | | | | | |
| 15 | 1 | 68.6 | 0.995 | 62.2 | 0.979 | 53.6 |
| 60 | 1 | 62.5 | 1 | 61.9 | 0.998 | 58.5 |
| 120 | 1 | 60.7 | 1 | 59.6 | 0.994 | 54.6 |
| 600 | 1 | 60.7 | 0.991 | 54 | 0.979 | 47.1 |

Table 1, above, demonstrates that dopant concentration also impacts electrode response.

The amount of time that the poly-3-methyl 2,5 thienylene coated electrode is doped also influences the working range and overall performance of the electrode. Table 1 illustrates that as well. For example, for an electrode with a poly-3-methyl-2,5-thienylene coating thickness of 30s that was doped in a 0.01M solution of potassium iodide at a doping potential of +0.7 volts vs. Ag/AgCl for about 60 seconds to 120 seconds, a substantially Nernstian response curve was obtained over a relatively wide working range.

Electrodes with a polythienylene coating thickness of about 500 Å to about 2,000 Å and doped in a $10^{-1}$M to about $10^{-2}$M solution of potassium iodide for about 15 seconds to about 600 seconds at a doping potential of about +0.6 volt to about +1 volt vs. Ag/AgCl exhibit a substantially linear correlation between the log of iodide ion concentration and potential readout in solutions with iodide concentrations of about $10^{-1}$M to about $10^{-7}$M. The slope of the response curves throughout the working range of these electrodes can vary, but usually is about 55 mV/decade to about 65 mV/decade. Electrodes that are coated with a conducting polymer and doped within these parameters are well suited for use in a sensitive potentiometric analysis for determining the concentration of iodide ion in solution by observing the electrical potential readout from the electrode.

These parameters are interdependent, however. For example, as the polymer coating thickness is increased, the amount of dopant in the polymer coating ($I_2$) must also be increased for equivalent response characteristics.

A greater amount of doping is required for relatively thicker films. Electrodes with poly-3-methyl-2,5-thienylene coating thicknesses of 30s, 60s and 90s were doped in an aqueous solution with a molar concentration of potassium iodide of 0.01 for 1 minute and 5 minutes at an electrical potential of +0.7 volts and their performance compared. The data are presented graphically in FIG. 1. As can be observed from FIG. 1, the Electrodes A and B (30s and 60s coatings, respectively) exhibited a straight slope response curve over the entire working range for electrodes that were doped for 1 or 5 minutes. The Electrode C, having the thickest coating (90s), exhibited a straight slope response only when doped for 5 minutes. Electrode C did not exhibit the desired Nernstian response when doped for only one minute.

EXAMPLE 1

Preparation of a Poly-3-Methyl-2.5-Thienylene Coated Electrode

Figure 2:
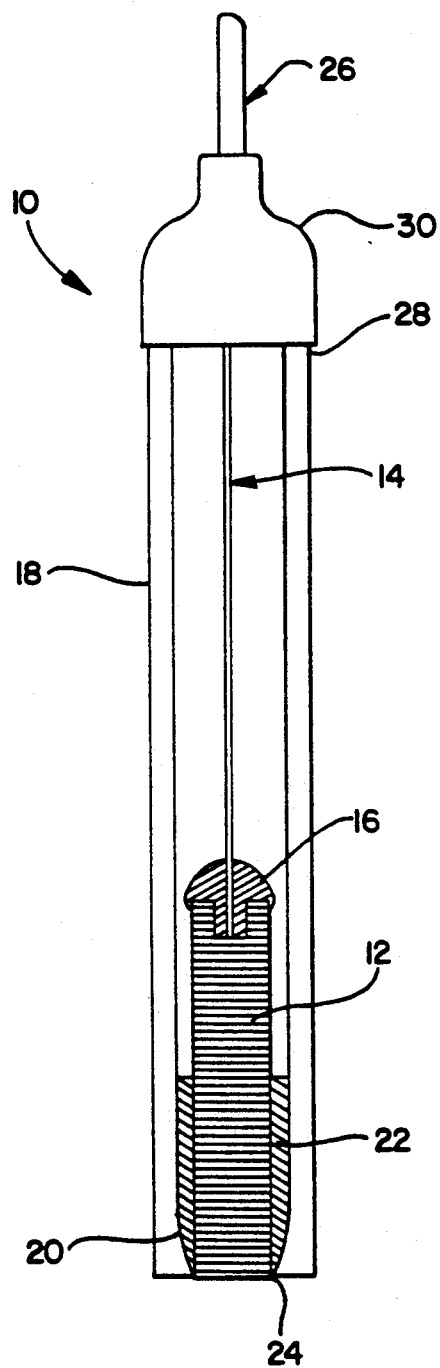
FIG. 2 is an elevation view of a coated electrode, partially broken away to show the interior portion of the electrode assembly.

An iodine-doped, poly-3-methyl-2,5-thienylene film coated electrode was prepared. FIG. 2 is a partial cutaway illustration of detector assembly 10 that uses such a film-coated working electrode made according to this invention. This working electrode included a spectroscopic grade graphite rod 12 obtained from Paco Graphite, Inc., Decatur, Tex. The graphite rod 12 was grade AXF-SQBL and had a diameter of 4.4 mm and was about 4 cm long. A copper wire 14 was inserted into one end of the rod and was affixed thereto with silver paste 16. The rod was inserted toward the tapered end 20 of a glass tube 18 with an inner diameter of 5.9 mm and sealed to the glass at 22 using Torr Seal obtained from the Varian Corporation.

The glass collar and the solidified resin were ground with coarse emery paper until the tip of the graphite 24 protruded therefrom. This exposed portion 24 of the electrode is the working surface thereof. A male pin 26 made of electrically conductive material was soldered to the copper wire at the top end 28 of the glass tube and the base (not shown) of the male pin 26 was secured to the glass with a piece of heat-shrunk Polyvinylchloride 30. The electrode 10 was then polished using a 600-grid acetone-wetted emery paper, followed by ultrasonification and repolishing with an acetone-wetted fine filter paper.

Working electrodes produced in the foregoing manner were evaluated by producing a background cyclic voltammogram in an aqueous 0.1M solution of $KNO_3$. Only those electrodes with similar backgrounds were utilized for the examples herein.

Figure 3:
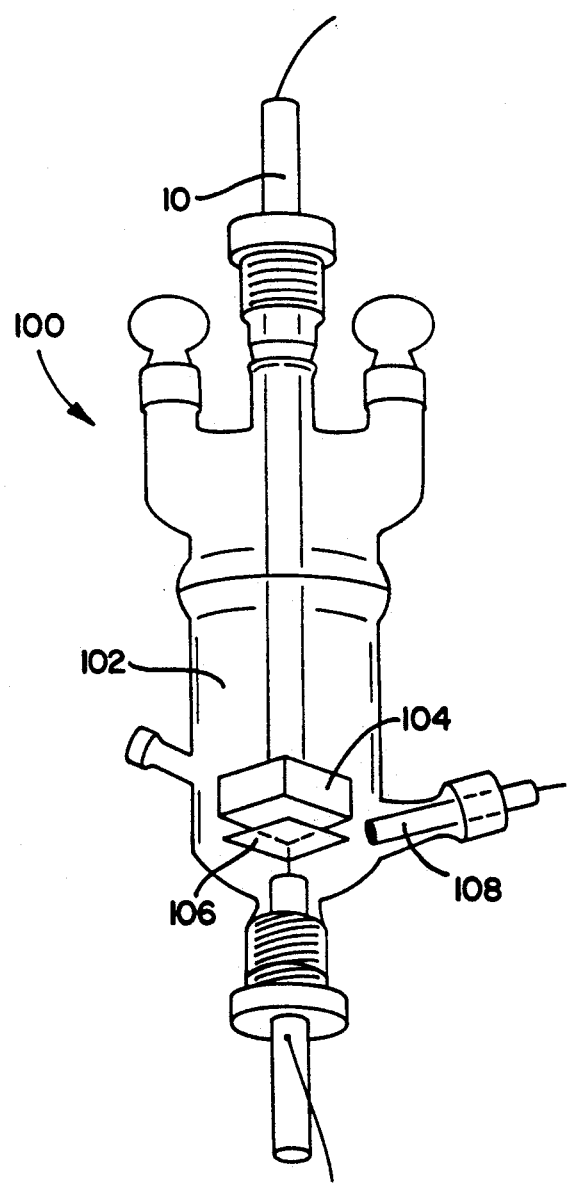
FIG. 3 is a perspective view of a single electrodeposition cell.

The working electrode was then utilized in a three-electrode single compartment electrodeposition cell 100 depicted generally in FIG. 3. The compartment 102 contained working electrode 104 and counter electrode 106 in a solution of 3-methylthiophene monomer (0.1M) and an electrolyte (tetrabutylammonium tetrafluoroborate; 0.1M) dissolved in an organic solvent (acetonitrile). The counter electrode was a 1"×1" platinum foil. The reference electrode 108 was an Ag/AgCl (3M NaCl). The Ag/AgCl electrode was a Model MF2020 electrode obtained from Bioanalytical Systems, Inc., West Lafayette, Ind.

The 3-methylthiophene monomer was polymerized on the graphite electrode under constant potential conditions of 1.65 volts vs. the Ag/AgCl electrode. The 3-methylthiophene monomer was polymerized onto the working surface 24 of the graphite electrode (FIG. 1). The obtained coated working electrode was then rinsed with an inert organic solvent (acetone), air dried for about 3 minutes and then immersed in another three-electrode single compartment cell similar to the one depicted in FIG. 3. The compartment 102 for this purpose contained an aqueous solution of potassium iodide. The iodide was oxidized and simultaneously doped into the poly-3-methyl-2,5-thienylene film as iodine ($I_2$) at an applied potential greater than about +0.6 volts. The electrode was then rinsed with water and dried in air for at least twenty minutes. The experimental conditions were those indicated in Table 1, above.

Iodide-selective electrodes manufactured according to the above detailed procedure were analyzed to determine their operating parameters and overall performance. Potential measurements in the following examples were made using an Orion Model 601A ionalyzer using an Orion Model 90-02 double junction reference electrode. A 10-percent by volume solution of nitric acid ($HNO_3$) was placed in the outer chamber of the reference electrode. The iodide selective electrode was connected to the ion alyzer with a coaxial cable. The electrodes were conditioned in a bath of agitated water until a steady potential reading resulted. The desired steady potential was achieved in about one-half to one hour.

The potassium iodide solutions used in the examples herein were prepared by diluting an aqueous solution of 1M KI. All test solutions used in the analyses detailed below contained 0.001M $HNO_3$ as an ionic strength adjuster except where interferences and the effect of solution pH on electrode performance were being investigated. Acetonitrile used in these examples was dried over a Type 4A molecular sieve. The 3-methylthiophene and tetrabutylammonium tetrafluoroborate (obtained from Aldrich Chemical Co.) were used as received and all other chemicals mentioned were made of analytical grade reagents that are commercially available. Distilled and deionized water were used throughout the examples, which were conducted at a temperature of 23°±0.5° C.

EXAMPLE 2

Uniformity Of Response Of Poly-3-Methyl-2,5-Thienylene Coated Iodide Ion Sensor Electrodes To determine the uniformity of electrode performance, electrodes were coated and doped under identical conditions and were evaluated to determine their response under controlled conditions. Each electrode evaluated had a film thickness of about 650 Å, obtained in 30 seconds.

Each coated electrode was doped in a 0.01M solution of KI with a 0.1M concentration of $NaNO_3$ as a supporting electrolyte therein for one minute at a doping potential of +0.7 volts vs. Ag/AgCl. The electrolyte enhances conductivity of the doping solution without providing interfering ions.

The response of each electrode was tested individually by placing the electrode in a cell which contained an aqueous solution of KI. The molar concentration of KI in solution varied from about 0.1 to about $1 \times 10^{-6}$. No voltage was applied during measurement.

The potential for each individual electrode for each KI solution and the mean potential and standard deviation for each KI solution prepared are reported in Table 2, below. This Table indicates a low standard deviation between the measurements made by each individual electrode. This condition, in turn, indicates that electrodes coated and doped under similar conditions perform uniformly.

TABLE 2

UNIFORMITY OF COATED ELECTRODE RESPONSE

| KI Concentration, M | Mean Potential, mV | Standard Deviation |
|---|---|---|
| $10^{-1}$ | 211 | 3.56 |
| $10^{-2}$ | 276 | 3.7 |
| $10^{-3}$ | 337 | 3.77 |
| $10^{-4}$ | 397 | 4.27 |
| $10^{-5}$ | 454 | 5.89 |
| $10^{-6}$ | 493 | 8.17 |

EXAMPLE 3

Figure 4:
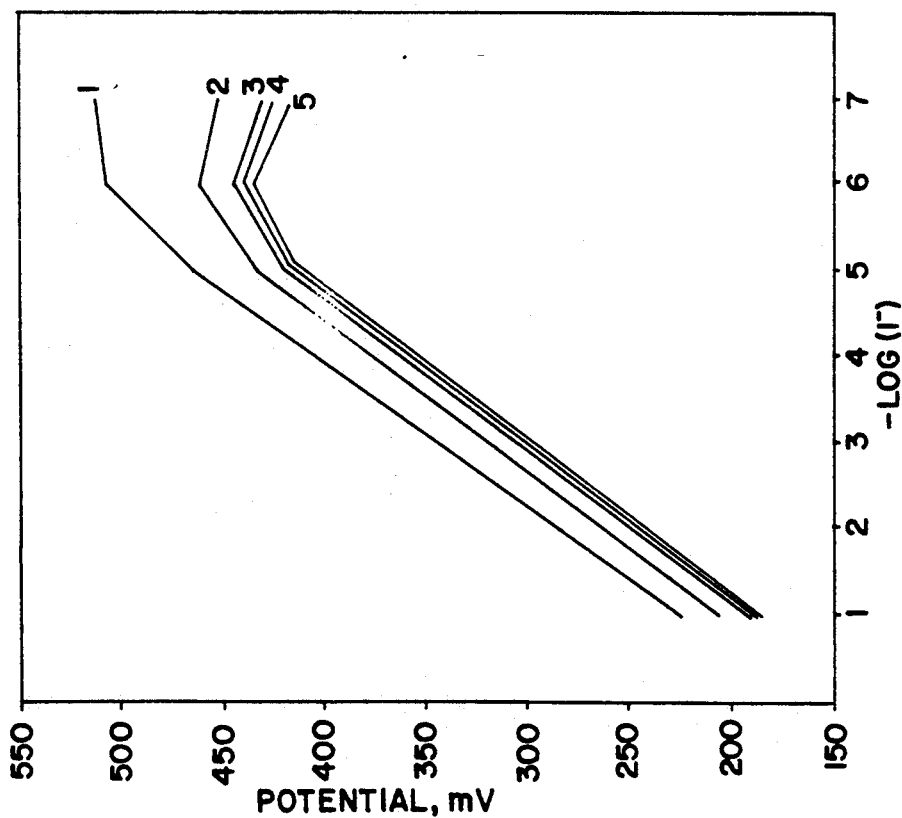
FIG. 4 is a graph that illustrates the stability of electrode response over time for electrodes embodying the present invention.

Stability Of Potential Measurements Made With Poly-3-Methyl-2,5-Thienylene Coated Iodide Ion Sensor Electrodes The effect of multiple runs on the measured electrical potential of an electrode coated and doped according to this invention is illustrated in FIG. 4. The polythienylene was polymerized onto the electrode as described above for 60 seconds to provide a coating about 1,200 Å thick. The polymer was then doped in a 0.01M aqueous solution of KI (in 0.1M $NaNO_3$) for 60 seconds. The electrode was placed in an aqueous solution of KI and the change in potential was recorded as a function of the concentration of KI in solution. The electrode was equilibrated in gently stirred, deionized water for at least 15 minutes prior to each run. In FIG. 4, Line 1 is the response curve of a freshly prepared electrode; Line 2 is the response curve of the same electrode after it was stored in a solution of 0.01M KI overnight; Line 3 is the response curve of the same electrode after it was kept in air overnight; Line 4 is the response curve of the same electrode after the electrode was stored in a 1M KI solution overnight; and Line 5 is the response curve of the same electrode after storage in a 1M KI solution for about 48 hours.

Although a parallel shift toward more positive potentials was noted with each successive run, the slope of the response curve did not change, especially in the molar iodide ion concentration range of 0.1 to $1 \times 10^{-5}$ which is substantially the entire working range of the electrode. The shift was more pronounced in solutions with an iodide ion concentration of less than $1 \times 10^{-5}$M, in which the response leveled off significantly.

This shift or drift in potential to lower values may be caused by leaching of $I_2$ from the polymer coating. This process apparently continues until a stable value for the amount of $I_2$ in the polymer is reached, or the rate of leaching slows to the extent that the equation $$E = \text{constant} - 0.0592 \log[I^-]$$

defines the slope of the response curve.

Table 3, below, illustrates that the potential shift observed in FIG. 4 does not occur if the second measurement immediately follows the first. After the potential was measured in each KI solution (column 1 in Table 3), the potential in the solution was remeasured by the same electrode immediately thereafter in the order reported in Table 3 (columns 2-5 in Table 3).

As can be observed by the values in parentheses, very little difference in potential was observed between the first and second measurements. Although time does effect the ability of the electrode to reproduce exactly a particular measurement in a solution of given iodide ion concentration, the electrode response remains Nernstian. Therefore, the response is predictable through most of the working range of the electrode even after several runs, without having to redope the polymer film.

TABLE 3

SHORT TERM DRIFT OF ELECTRODE POTENTIAL[1]

| KI Concentration (M) | Measurement [mV vs. Ag/AgCl] | | | | |
|---|---|---|---|---|---|
| | 1 | 2 | 3 | 4 | 5 |
| $10^{-5}$ | 415 | | 413(2) | | |
| $10^{-4}$ | 366 | | | | 364(2) |
| $10^{-3}$ | 314 | 314(0) | | | |
| $10^{-2}$ | 263 | | | 263(0) | |

[1]The numbers in parentheses refer to the difference in potential between the first and second measurement at the respective concentration level.

EXAMPLE 4

Selectivity Of Poly-3-methyl 2,5-Thienylene Coated Iodide Ion Sensor Electrode

Table 4, below, summarizes the selectivity coefficients of various anions of the poly-3-methyl-2,5-thienylene coated iodide ion sensor electrode. The electrode used to determine the selectivity coefficient in Table 4 has a 60s film having a thickness of about 1,200 Å.

The polymer was doped in an aqueous solution of 0.01M KI at a doping potential of +0.7 volts vs. Ag/AgCl for 90 seconds. The selectivity coefficients for most anions is on the order of $10^{-3}$ or less. These anions, if present, are likely to cause little interference in the potential readout.

TABLE 4

SELECTIVITY COEFFICIENTS OF THE POLYTHIENYLENE COATED ELECTRODE

| Anion (x) | Selectivity Coefficient Potential, $k_{I,x}$ |
|---|---|
| Chloride | $1.37 \times 10^{-3}$ |
| Bromide | $3.81 \times 10^{-3}$ |
| Nitrate | $3.22 \times 10^{-3}$ |
| Perchlorate | $3.2 \times 10^{-3}$ |
| Acetate | $3.94 \times 10^{-3}$ |
| Formate | $1.11 \times 10^{-3}$ |
| Thiocyanide | $2.67 \times 10^{-3}$ |
| Dihydrogen phosphate | $3.86 \times 10^{-4}$ |
| Cyanide | 0.45 |
| Hydroxide | 0.08 |
| Carbonate | $3.69 \times 10^{-3}$ |
| Sulfate | $3.67 \times 10^{-4}$ |
| Thiosulfate | $3.82 \times 10^{-3}$ |
| Tartarate | $6.35 \times 10^{-5}$ |
| Citrate | $5.61 \times 10^{-4}$ |

The relatively high selectivity coeffeicients obtained for $OH^-$ and $CN^-$ anions is believed to be due to the presence of $I_2$ in the film matrix with which these ions react. Thus, the amount of iodine in the film will decrease while the iodide ion in the aqueous phase increases if these ions are present in the solution. This causes a shift in the electrode potential to a lower value and it will be interpreted as interference by the sensor. Generally, any oxidation/reduction system which can reduce iodine or oxidize iodide interferes with measurements made by the electrodes disclosed herein.

EXAMPLE 5

Response Time Of The Thienylene Coated Electrode

The response time of a poly-3-methyl-2,5-thienylene coated electrodes was observed by injecting a small amount of concentrated iodide solution ($10^{-1}$M KI) into a gently stirred solution of 0.001M $HNO_3$ in which the coated electrodes were conditioned. The potential changes vs. Ag/AgCl were recorded on a strip chart. The elapsed time between injection of the iodide solution and a new potential plateau was accepted as response time. For test solutions with iodide concentrations greater than $1 \times 10^{-4}$M, the response time was observed to be less than 20 seconds. For test solutions with iodide concentrations of less than $1 \times 10^{-4}$M, the response time was observed to be around 40 seconds.

EXAMPLE 6

The Effect Of Solution pH On Electrode Response

Figure 5:
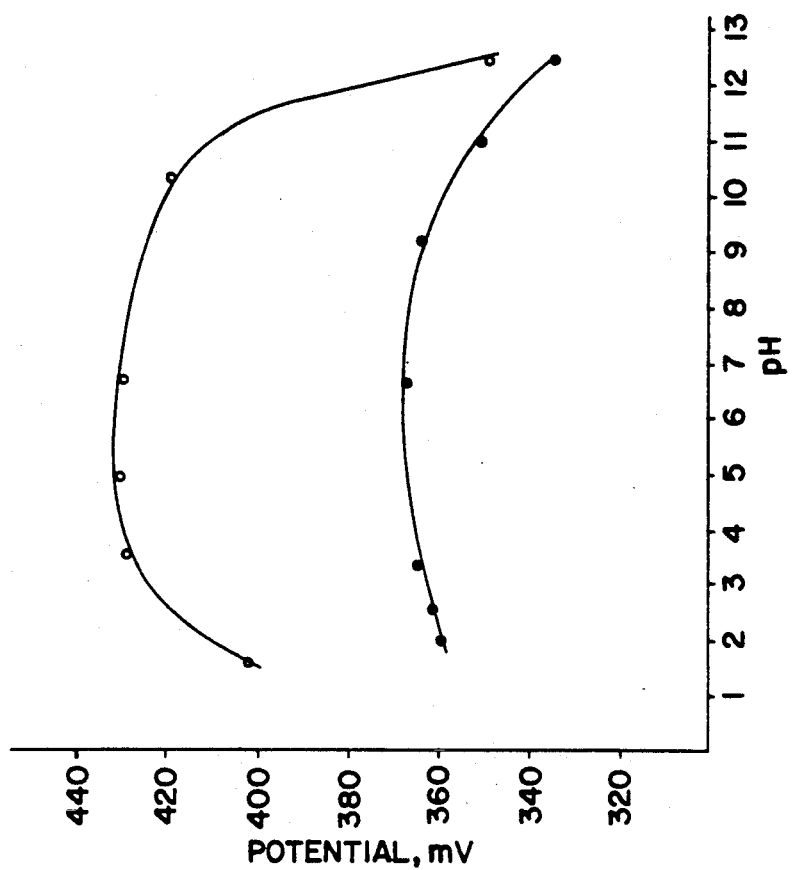
FIG. 5 is a graph that illustrates the effect of the solution pH on electrode response.

The pH of the iodide solution was found to impact electrode response somewhat. Poly-3-methyl-2,5-thienylene coated electrodes with a 60 second coating were doped in an aqueous solution with a 0.01M concentration of KI (in 0.1M $NaNO_3$) for 90 seconds at a voltage of about 0.7 volts vs. Ag/AgCl. The potential response of these electrodes was examined at varying pH's in aqueous solutions with 0.01 and 0.001M concentrations of KI. The pH of these solutions was adjusted by adding either $HNO_3$ or NaOH as needed. As illustrated in FIG. 5, the operating pH for the electrode is about 3.5 to about 10 in solutions with a KI concentration of about 0.0001M (open circles,○) and about 2 to about 10 in solutions with a KI concentration of about 0.01M (closed circles, ).

The foregoing discussion is intended to illustrate the invention and exemplify the general principles disclosed herein. However, this description is not to be interpreted as limiting the invention which is subject to many variations and modifications within the scope and spirit thereof as will be understood by one skilled in the art.

We claim:

1. An electrode for an iodide ion potentiometric sensor comprising:

a base electrode having an iodine-doped polythienylene coating on a working surface thereof, the thickness of the polythienylene coating and the extent of iodine doping being sufficient to provide electrode response of about 55 mV/decade to about 65 mV/decade when the poly(thienylene) coated portion of the electrode is placed in an aqueous solution having an iodide concentration of about $10^{-1}$M to about $10^{-7}$M.

2. The electrode of claim 1 wherein the base electrode is an inert material.

3. The electrode of claim 2 wherein the inert material is a carbonaceous material.

4. The electrode of claim 3 wherein the carbonaceous material is graphite.

5. The electrode of claim 3 wherein the carbonaceous material is glassy carbon.

6. The electrode of claim 2 wherein the inert material is platinum.

7. The electrode of claim 2 wherein the inert material is a conductive metal oxide.

8. The electrode of claim 7 wherein the metal oxide is tin oxide.

9. The electrode of claim 1 wherein the polythienylene is poly-3-alkylthienylene.

10. The electrode of claim 9 wherein the poly-3-alkylthienylene is poly-3-methyl-2,5-thienylene.

11. The electrode of claim 1 wherein the thickness of the polythienylene coating on the electrode is about 200 Å mm to about 3,000 Å mm.

* * * * *